(12) United States Patent
Detraz et al.

(10) Patent No.: US 7,829,323 B2
(45) Date of Patent: Nov. 9, 2010

(54) MIXING DEVICES FOR CHEMICAL LYSIS OF CELLS

(75) Inventors: Noel Joseph Francois Detraz, Lyons (FR); Guillaume Rigaut, Lyons (FR)

(73) Assignee: Merial Limited, Duluth, GA (US)

( * ) Notice: Subject to any disclaimer, the term of this patent is extended or adjusted under 35 U.S.C. 154(b) by 410 days.

(21) Appl. No.: 11/287,906

(22) Filed: Nov. 28, 2005

(65) Prior Publication Data

US 2006/0166307 A1 Jul. 27, 2006

Related U.S. Application Data

(60) Provisional application No. 60/631,782, filed on Nov. 30, 2004.

(51) Int. Cl.
 *C12P 1/00* (2006.01)
 *C12N 1/06* (2006.01)
(52) U.S. Cl. .......................................... 435/259; 435/41
(58) Field of Classification Search .................. 435/41, 435/259
See application file for complete search history.

(56) References Cited

U.S. PATENT DOCUMENTS

| | | | | |
|---|---|---|---|---|
| 5,837,529 A | * | 11/1998 | Wan et al. | 435/259 |
| 6,686,195 B1 | | 2/2004 | Colin et al. | 435/306.1 |
| 6,942,169 B2 | | 9/2005 | Sparks | 241/1 |
| 2001/0034435 A1 | * | 10/2001 | Nochumson et al. | 536/23.1 |

FOREIGN PATENT DOCUMENTS

GB        2338236 A   * 12/1999

* cited by examiner

*Primary Examiner*—Jon P Weber
*Assistant Examiner*—Kailash C Srivastava
(74) *Attorney, Agent, or Firm*—Judy Jarecki-Black; Merial Limited; Chad Kitchen

(57) ABSTRACT

The invention relates to flow-through devices for mixing fluids and uses thereof for mixing and for lysing cells to release biological compounds of interest. The invention particularly encompasses flow-through methods for mixing and chemical methods for the isolation and purification of plasmid DNA from cell culture.

7 Claims, 5 Drawing Sheets

MIXING DEVICES FOR CHEMICAL LYSIS OF CELLS

INCORPORATION BY REFERENCE

This application claims priority to U.S. Provisional Application Ser. No. 60/631,782 filed Nov. 30, 2004, the disclosure of which is incorporated by reference in its entirety.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to flow-through devices for mixing fluids, notably lysing solutions or lysis solutions and fluids containing cells to be lysed. The present invention provides flow-through methods for mixing and for lysing cells in order to release biological compounds of interest. Specifically, the present invention relates to flow-through methods for mixing and chemical methods for lysing cells to release plasmids.

BACKGROUND OF THE INVENTION

In the field of recombinant deoxyribonucleic acids (DNA) technology, plasmids are largely used to encode and express heterologous proteins of interest.

Recently, it has been shown that plasmid DNA may be useful for clinical applications, such as gene therapy and genetic immunization (Wolf et al., Science, 1990, 247, 1465-1468; WO-A-90/11092).

Plasmids are too large and complex to be produced in large quantities through synthetic means. Instead, plasmids must be produced in cells, and subsequently extracted, harvested and purified. Generally, plasmids are produced via bacterial fermentation and recovered by cell disruption. The persons skilled in the art know the fermentation techniques. Many of these techniques have been published and are routinely used (e.g. Sambrook et al., section 1.21, "Extraction and purification of plasmid DNA", Molecular Cloning: a laboratory manual, second edition, cold Spring Harbor Laboratory Press, 1989). These methods involve the growth of the bacterial culture and replication of the plasmid, harvesting and lysis of the bacteria, isolation and purification of the plasmid DNA.

Accordingly, there is a need for large scale processes for extracting and recovering supercoiled plasmid DNA.

A large variety of cell disruption techniques is available, including mechanical or physical (e.g. high pressures, sonication, heat treatments), chemical (e.g. nonionic detergents, ionic detergents, organic solvents, alkali), or enzymatic (e.g. lysozyme) methods.

For pharmaceutical and immunization uses, plasmid DNA compositions must avoid the presence of impurities, such as genomic DNA, endotoxins and tRNA (transfer ribonucleic acids) or rRNA (ribosomal ribonucleic acids), and a decrease of yield due to a plasmid degradation and to the low-efficiency of the extraction method.

As supercoiled plasmid DNA is usually separated from both the larger host cell genomic DNA and from the smaller cellular RNAs and DNAs on the basis of their size, it is important to avoid shearing either the plasmid DNA or the genomic DNA. Shearing forces may damage genomic DNAs and produce genomic DNAs having the same size than plasmid DNAs. Shearing forces may also cut the plasmid DNAs and produce linearized plasmid DNAs. Linearized plasmid DNAs and genomic DNA fragments similar in size to the supercoiled plasmid DNAs may be particularly difficult to be separated from supercoiled plasmid DNAs.

For pharmaceutical and immunization uses, it is preferable to use supercoiled plasmid DNAs, which are smaller and more compact than relaxed closed circular plasmid DNAs and less vulnerable to enzymatic degradation. Cell disruption techniques may damage supercoiled plasmid DNAs and produce closed circular, linearized or fragmented plasmid DNAs, which increase the level of impurities and reduce the yield of supercoiled plasmid DNAs.

Several cell disruption techniques are commonly used to release intracellular product, particularly intracellular proteins.

Cell disruption techniques are classified into two main categories: the first one involves only physical forces to break the cells and the second one involves contact of chemical or enzymatic agents with the cells and destruction of the cell membrane, capsule or wall.

The physical forces involved in the first category may be:

high pressures or high temperatures (for example due to microfluidization, nebulization techniques or heat treatments), cavitation (for example due to sonication techniques), impacts against solids (for example due to bead milling techniques) (e.g. see U.S. Pat. No. 6,455,287; Agerkvist I. et al., Biotechnol. Bioeng., 1990, 36, 1083-1089; U.S. Pat. No. 6,071,480).

The cell disruption depends on the conditions of residence time, pressure, temperature, agitation rate, shearing forces, impact forces . . . . These conditions are difficult to control and to monitor. Too weak physical forces may not break all the cells and lead to a non-optimal yield of plasmid DNAs. Too strong physical forces may damage free DNAs and lead to plasmid DNA fragmentation, create an unacceptable level of impurities and reduce the yield of supercoiled plasmid DNAs.

In the second category of cell disruption techniques, the enzymatic or chemical lysis of cells involves the mixing between the cell suspension and the lysing solution. This constitutes the technical field of the present invention. The mixing between the cell suspension and the lysing solution is a crucial step. Incomplete mixings, in particular due to a too short time of mixing, may result in an incomplete lysis of the cells, in a partial loss of the biological compound of interest, leading to non-optimal yield. On the contrary, a too long time of mixing may result in a too long contact between the cells and lysing solution, lead to the degradation of the biological compound of interest and of the genomic DNAs, produce genomic DNA fragments having the same size as the plasmid DNAs. Both situations will increase the costs of the biological final compound of interest. It is acknowledged in the prior art that to allow a full recovery of supercoiled plasmid DNAs, processing conditions must be very mild, particularly with respect to shearing forces during the mixing step.

U.S. Pat. No. 6,197,553 describes enzymatic lysis with lysozyme and heat treatment through a heat exchanger. This technique has the disadvantage of using 2 types of enzymes (lysozyme and RNase) and that the enzymes are from animal sources, which could lead to possible problems of safety due to contamination, among others by prions. Another disadvantage of this technique is that the enzymes must be subsequently discarded. This involves several purification steps, in particular gradient-based anion exchange chromatography and gradient-based reverse phase high performance liquid chromatography.

To automate the methods for purifying plasmid DNAs from cell, it has already been proposed to continuously pass the cell suspension to be lysed with a lysing solution through a static mixer (WO-A-00/05358). Usually, static mixers contain an internal helical structure which allows the cell suspension and the lysing solution to come into contact in an opposite rotary flow and force them to mix in a turbulent or laminar flow. Such mixers are described, for instance, in WO-A-00/05358 and U.S. Pat. No. 5,837,529. The technique using static mixer is difficult to scale-up due to the limits of internal diameter size and flow rates.

Others propose to continuously pass the cell suspension to be lysed and a lysing solution through a common tube (see U.S. Pat. No. 6,664,049). A major disadvantage of this technique is the great difficulty to scale-up due to the small size of the internal diameter of the tube. The solution described in this patent is not to scale-up the process but to multiply the tubes to increase the production. This solution requires a complex installation with multiple tubes and one or several pumps. This installation is difficult to control and to monitor, particularly to adjust the flow rates in each tube in order to obtain and to keep an efficient mixing.

There is a need for new scalable methods to prepare purified biological compounds of interest, in particular purified plasmid DNAs, and more particularly purified supercoiled plasmid DNAs.

These methods may have a high yield and produce biological compounds of interest with a good level of purity. It is also desirable to have scalable methods that can be used to produce large quantities of plasmid DNAs. These methods may also be fast, easy to use and easy for maintenance.

In addition, it is desirable to have flow-through methods to increase the robustness, reproducibility and ease of scale-up. It is desirable to have methods in two steps, the mixing step and the contact step, in order to control and to monitor them separately. It is desirable to have methods that can produce plasmid DNAs at a low cost. It is also desirable to prepare purified plasmid DNAs, without toxic chemicals, impurities, endotoxins or other compounds that would be prejudicial for their safety, efficacy or purity.

One of the objectives of the invention is to provide a flow-through and scalable method of mixing at least two fluids to allow chemical lysis of the cells suspended in one of these fluids.

A second objective of the invention is to propose a mixing device for such method.

A third objective of the invention is to provide a flow-through and scalable method for preparing biological compounds of interest, in particular supercoiled plasmid DNAs, using such a mixing device.

The present invention meets these needs and reaches these objectives.

Citation or identification of any document in this application is not an admission that such document is available as prior art to the present invention.

SUMMARY OF THE INVENTION

A first object of the present invention is a flow-through device for mixing a lysing solution and/or lysis solution with one or more additional fluids, such as a sample material, wherein at least one of the additional fluids comprises suspended cells to be lysed, said device comprising:

a conduit through which the lysing solution circulates with a linear speed equal to or less than about 2 m/sec;

one or more pipes through which one or more additional fluids are injected into the conduit with a linear speed from about 1 m/sec to about 150 m/sec, wherein the ratio between the additional fluid linear speed and the lysing solution linear speed measured at the pipe outlet is from about 100 to about 15000 and causes substantial mixing of the lysing solution with one or more additional fluids; and an outlet through which a outgoing fluid comes out of the conduit, wherein the outgoing fluid is composed of the lysing solution and one or more additional fluids after having been substantially mixed.

A second object of the present invention is a flow-through device for mixing a lysing solution with one or more additional fluids, wherein at least one of the additional fluids including suspended cells to be lysed, comprising:

a conduit through which the lysing solution circulates with a linear speed equal to or less than about 2 m/sec;

one or more pipes through which one or more additional fluids are injected into the conduit with a linear speed from about 1 m/sec to about 150 m/sec, wherein the ratio of linear speeds measured at the pipe outlet between the additional fluid linear speed and the lysing solution linear speed is from about 100 to about 15000 and causes substantial mixing of the lysing solution with one or more additional fluids, for example, a sample material;

an outlet through which a outgoing fluid comes out of the conduit, wherein the outgoing fluid is composed of the lysing solution and one or more additional fluids after having been substantially mixed; and a vortex reducer located near or in the outlet of the conduit, which reduces or suppresses any rotational velocity or any toric component of the outgoing fluid to obtain an outgoing laminar flow.

Still another object is a flow-through method for preparing a biological lysate containing a biological compound of interest, comprising:

flow of a cell suspension and a lysing solution through a mixing device according to the invention to allow substantially a complete mixing and a cell lysis without a permanent denaturing of the biological compounds of interest;

flow of the mixed fluids through an optional contact pipe to allow degradation of impurities;

neutralize the lysing solution by adding a neutralizing solution.

A further object of the invention is a scalable and flow-through alkaline lysis process for large scale plasmid DNA extraction, comprising:

flow of a cell suspension and an alkaline lysing solution through a mixing device according to the invention to allow substantially a complete mixing and a cell lysis without a permanent denaturing of the plasmid DNAs;

flow of the mixed fluids through an optional contact pipe to allow degradation of impurities;

neutralize the lysing solution by adding a neutralizing solution;

precipitate the impurities by adding a precipitating solution;

clarify the lysate by decantation and/or centrifugation and/or filtration.

Still another objects of the invention are the biological compounds of interest, particularly the plasmid DNAs obtained by the process of the invention.

It is noted that in this disclosure and particularly in the claims, terms such as "comprises", "comprised", "comprising" and the likes can have the meaning attributed to them in U.S. patent law; e.g., they can mean "includes", "included", "including", and the likes; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF DRAWINGS

The following Detailed Description, given by way of example, and not intended to limit the invention to specific embodiments described, may be understood in conjunction with the accompanying Figures, incorporated herein by reference, in which.

DETAILED DESCRIPTION OF THE INVENTION

The present invention concerns a flow-through device for mixing a lysing solution with one or more additional fluids, wherein at least one of the additional fluids comprises suspended cells to be lysed.

Figure 1:
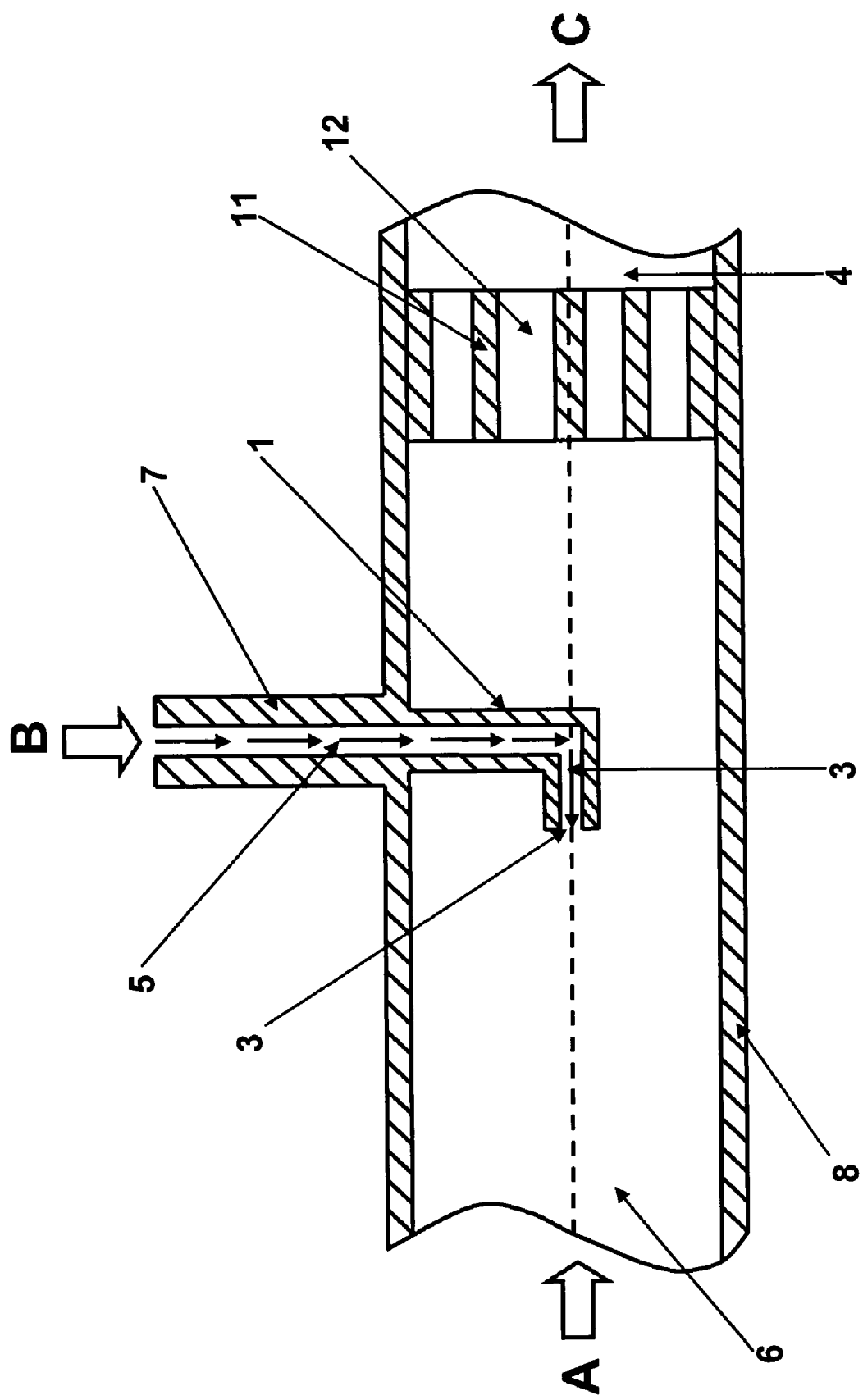
FIG. 1. illustrates a longitudinal section view of a mixing device with a counter-flow pipe outlet and a vortex reducer, wherein A indicates the lysing solution, B the additional fluid and C the mixed fluids.

As shown in FIG. 1, a device is provided for injecting one or more additional fluids through one or more pipes [1] into a directional moving flow of the lysing solution through a conduit [2].

By definition, the conduit [2] has a larger cross section than the pipe [1], in order to place the pipe [1] inside the conduit [2]. Preferably, the conduit [2] and the contact pipe have a cross section capable to induce laminar flow to the fluids circulating through them.

A cross section of a pipe, conduit or vortex reducer is by definition the section perpendicular to the direction of the flow circulating through this pipe, conduit or vortex reducer. Hereunder the term of section is used for cross section.

There is no restriction to a particular form of the conduit [2] or of the pipe [1], in particular in the forms of their sections such as, but not limited to, cylindrically-shaped or squarely-shaped.

The lysing solution circulates into the conduit with a linear speed equal to or less than about 2 m/sec, preferably equal to or less than about 0.2 m/sec, and more preferably equal to or less than about 0.04 m/sec, measured at the pipe outlet [3]. The lysing solution preferably flows with a linear speed capable to induce a laminar flow. A value of a Reynolds number inferior to 2000 characterizes a laminar flow. One skilled in the art is able to calculate the Reynolds number of a circulating fluid.

The linear speed of a fluid according to the present invention is calculated by dividing the volumetric flow rate by the surface area of the cross-section of the channel, notably of the pipe [1] or conduit [2], and is expressed in meter per second (m/sec).

As shown in FIG. 1, the pipe(s) is located within a conduit [2] having an upstream inlet [6] and a downstream outlet [4].

The lysing solution is entering into the mixing device according to the invention through the upstream inlet [6] of the conduit [2]. The additional fluids are entering into the mixing device according to the invention through the pipe(s) [1]. The mixed fluids come out of the mixing device according to the invention through the downstream outlet [4] of the conduit [2].

The pipe ends with an outlet [3] preferably aligned with longitudinal axis of the conduit [2]. The pipe outlet [3] may also be aligned with another direction, inside the conduit [2], for example directed to the conduit wall [8] (not shown).

Figure 2:
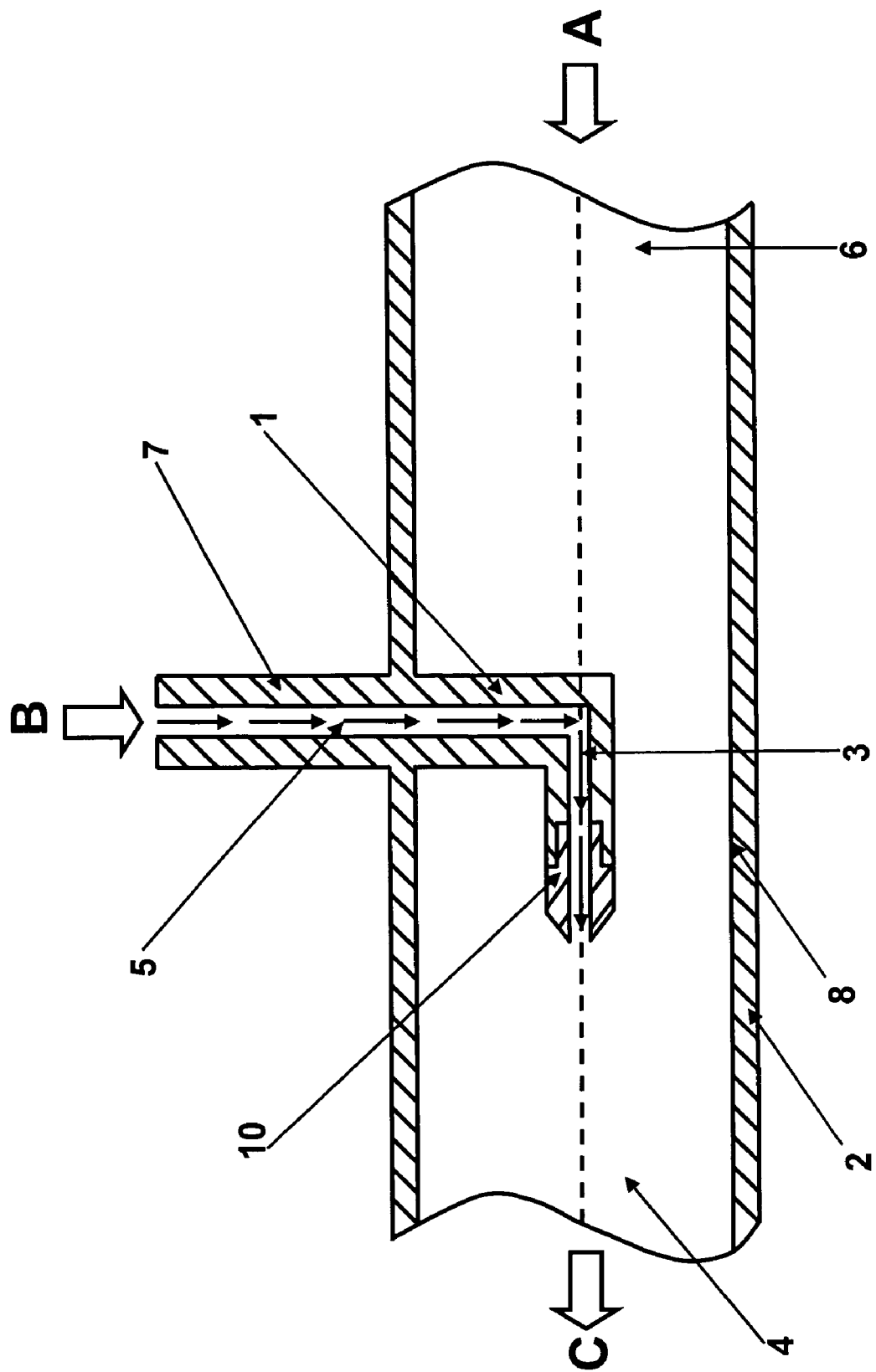
FIG. 2. illustrates a longitudinal section view of a mixing device with a co-flow spray nozzle, wherein A indicates the lysing solution, B the additional fluid and C the mixed fluids.
Figure 3:
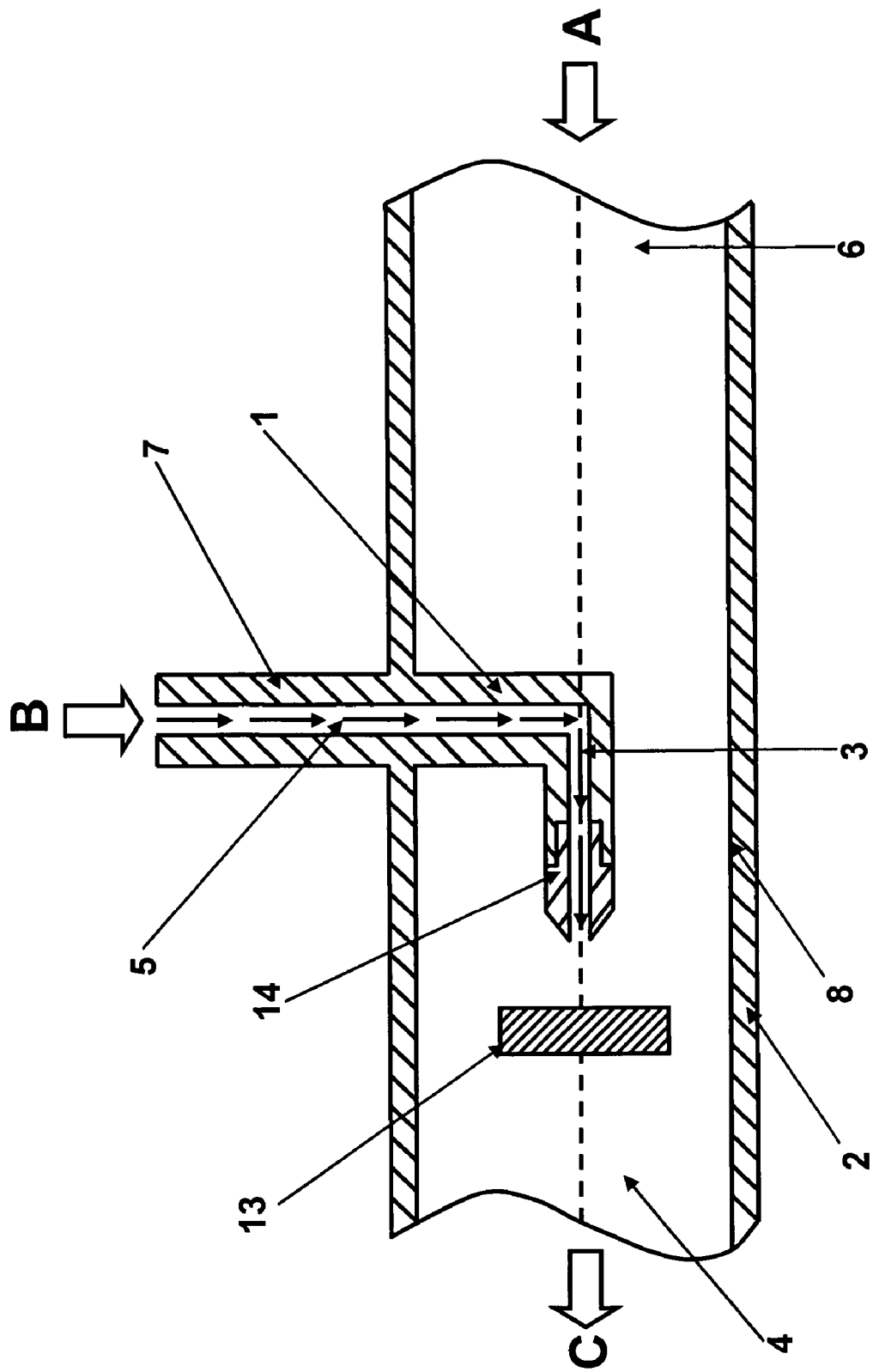
FIG. 3. illustrates a longitudinal section view of a mixing device with a co-flow impact spray nozzle, wherein A indicates the lysing solution, B the additional fluid and C the mixed fluids.
Figure 5:
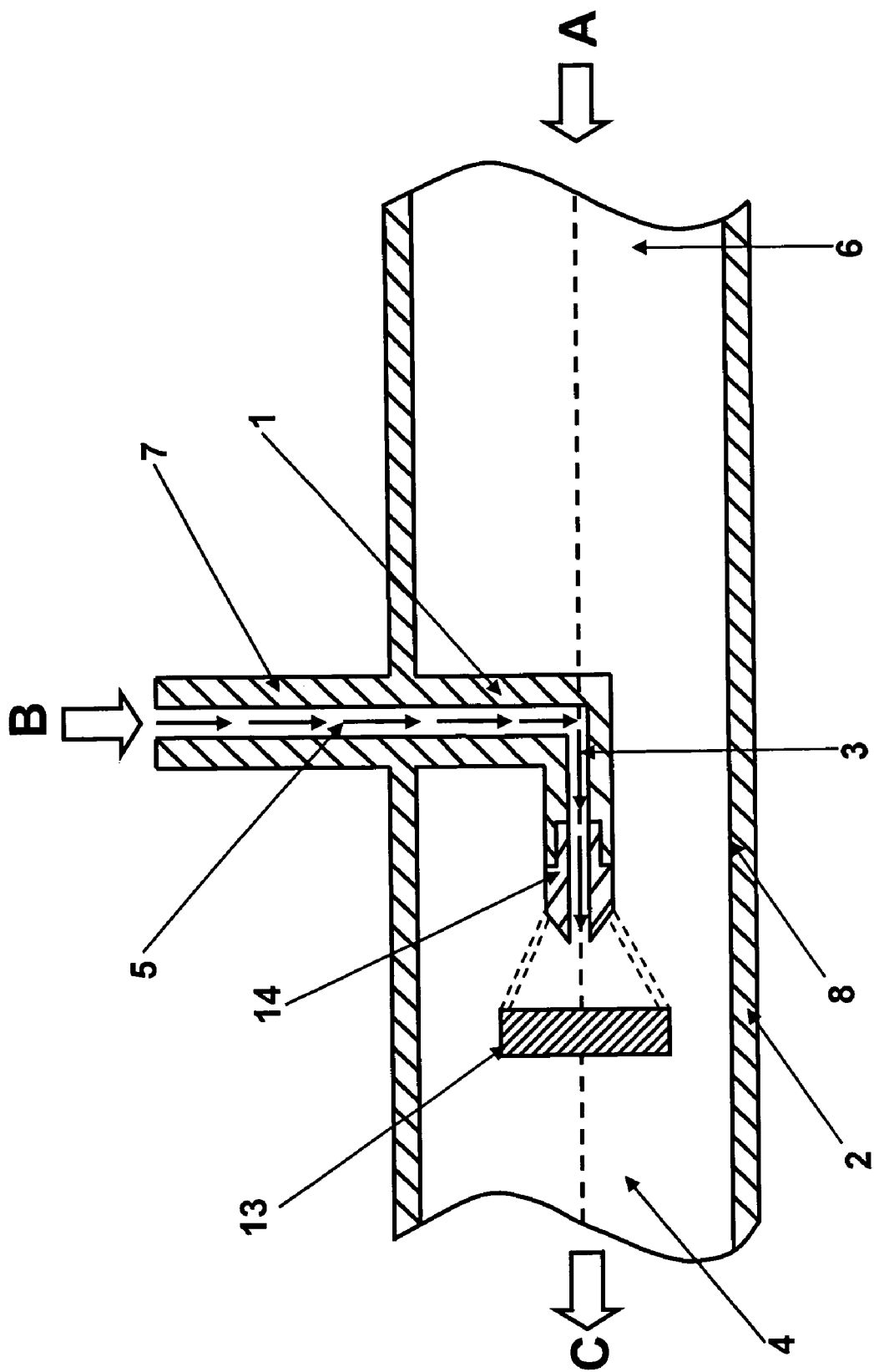
FIG. 5. illustrates a spray nozzle with the impact plate attached.

The conduit [2] is provided with longitudinal axis as well as a section. One or more pipes [1] are connected to this conduit [2]. The outlet [3] of these pipes is provided for injecting one or more additional fluids in a direction opposite to the flow of the lysing solution (counter-flow injection). Alternately, the outlet [3] of these pipes is provided for injecting one or more additional fluids in the same direction as the flow of the lysing solution (co-flow injection) as shown in FIGS. 2, 3, 5.

The additional fluid is injected through the pipe outlet [3] with a linear speed from about 1 m/sec to about 150 m/sec, preferably from about 5 m/sec to about 50 m/sec, and more preferably from about 10 m/sec to about 20 m/sec, measured at the pipe outlet. The additional fluid preferably circulates with a linear speed capable to induce an additional fluid turbulent flow. A value of a Reynolds number superior to 3000 characterizes a turbulent flow.

The additional fluid is provided to the pipe outlet [3] via a feed leg [7] radially emanating from the side wall [8] of the conduit [2]. Through radial feed leg [7] is provided the additional fluid, generally cell suspension in communication with a bore [9] located along longitudinal axis of the conduit [2] for discharge of a flow of cell suspension into the moving lysing solution.

The mixing device according to the present invention stands between the upstream inlet [6] of the conduit [2] near the feed leg [7] or the pipe outlet [3] and the downstream outlet [4] (immediately after a vortex reducer if present, or immediately before a contact pipe if present, or immediately before a connector for addition of a neutralizing solution).

The linear speeds of the lysing solution and of the additional fluid(s) are chosen to provide a ratio between the additional fluid linear speed and the lysing solution linear speed from about 100 to about 15000, in particular from about 100 to about 5000, more particularly from about 100 to about 2000, preferably from about 300 to about 1000 and more preferably from about 400 to about 700. This ratio is calculated by dividing the additional fluid linear speed value by the lysing solution linear speed value.

The flow rate ratio between the additional fluid and the lysing solution is from about 0.1 to about 10, preferably from about 0.3 to about 3, and more preferably equal to 1.

The linear speeds of the lysing solution and the additional fluid are such that the flow of the additional fluid through the pipe outlet [3] induces shearing forces and turbulences causing a substantially complete mixing of fluids. The mixing is substantially completed, in about 10 seconds or less, preferably in about 5 seconds or less, more preferably in about 2 seconds or less.

The present invention allows in a continuous flow-through mode to submit the additional fluid(s) containing cell suspension to an intense shearing during a very short time to mix the cells and the lysing solution and to lyse the cells.

In fact shearing forces are applied on the cells only during the injection of the cell suspension through the pipe outlet [3].

The continuous flow-through mode of the present invention compared to a batch mode has the advantage of avoiding dead spaces inside the turbulence system (e.g. all the cells pass through the mixing zone and are submitted to shearing forces for an efficient mixing). It also limits the cells to a unique passage inside the mixing zone (e.g. no possibility for the cells to pass twice through the pipe outlet of the mixing device). The absence of mechanical parts inside the mixing device is also an advantage for the present invention.

In a preferred embodiment, the mixing device of the invention is composed of a conduit [2] having an upstream inlet [6] and a downstream outlet [4], a pipe [1] with an inlet [5] and an outlet [3] aligned with longitudinal axis of the conduit [2] and directed in co-flow or in counter-flow direction.

As shown in FIG. 2, in another preferred embodiment of the invention, the pipe outlet [3] ends by a spray nozzle [10]. By definition, a spray nozzle allows the dispersion of a fluid into a gas and the increase of the surface area of the fluid by the formation of small droplets. Many spray nozzles are available on the market (e.g. from Delavan® Spray Technologies; Spraying Systems Co.®; Bete® Fog Nozzle Inc.; PNR America LLC; Steinen Wm. Mfg. Co.; Nozzle Network Company Ltd.). One skilled in the art is able to select a spray nozzle and to use it according to the invention in a liquid environment, e.g. for the injection of a fluid into a second fluid. According to this preferred embodiment, the mixing device of the invention is composed of a conduit [2] having an upstream inlet [6] and a downstream outlet [4], a pipe [1] with an inlet [5] and an outlet ending by a spray nozzle [10] aligned with longitudinal axis of the conduit [2] and directed in co-flow (FIG. 2) or in counter-flow direction.

When a spray nozzle is used, the ratio of linear speed of the additional fluids to the linear speed of the lysing solution is from about 100 to about 6000, in particular from about 100 to about 3000, more particularly from about 100 to about 2000, preferably from about 300 to about 1000 and more preferably from about 400 to about 700.

Figure 4:
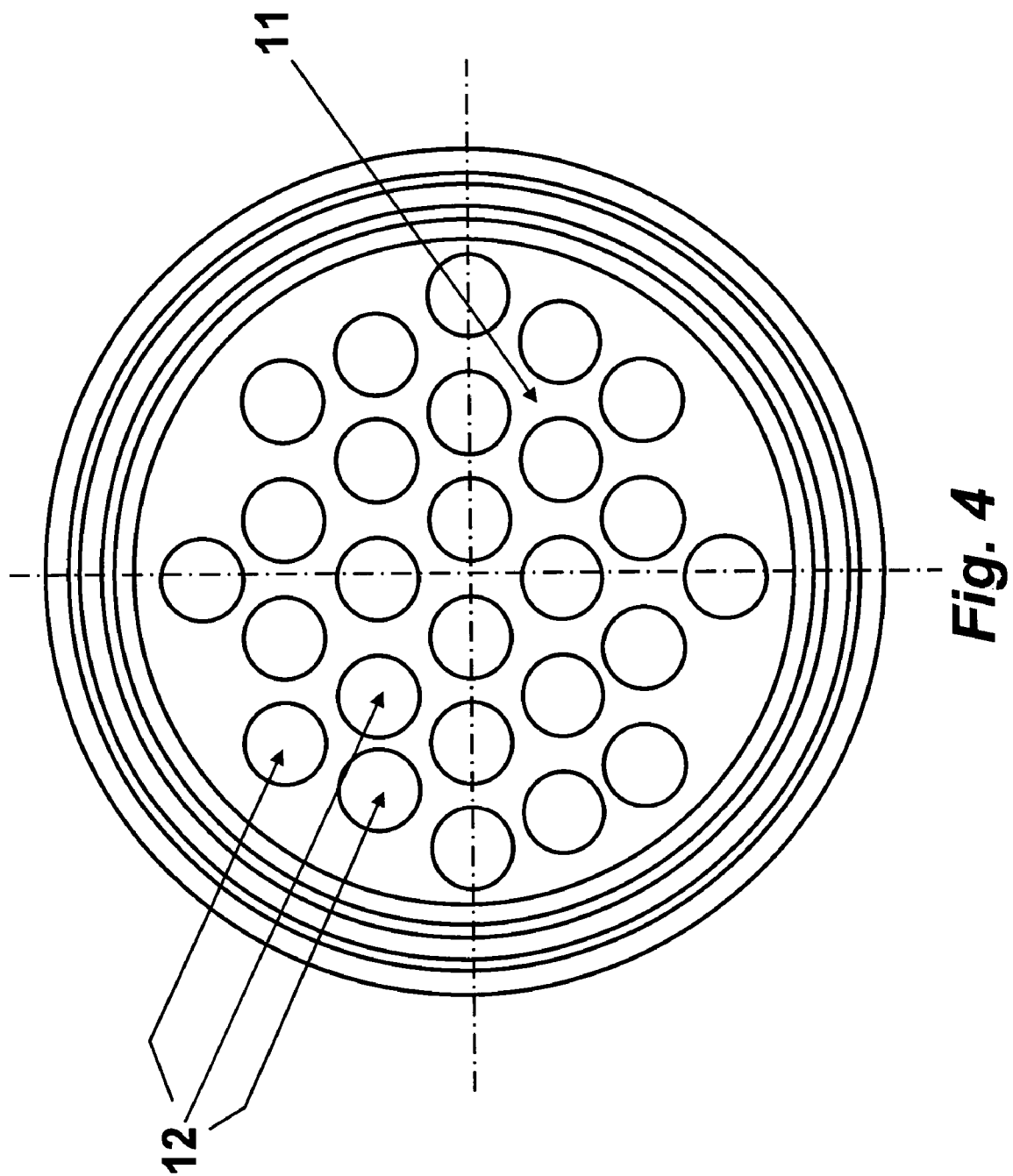
FIG. 4. illustrates a front view of a vortex reducer.

After mixing step by the device of invention the mixed fluids go through a vortex reducer to reduce or suppress any rotational velocity or any toric component of the flow and to obtain a laminar flow. The vortex reducer may be composed of any static device that reduces or suppresses any rotational velocity or any tonic component of a fluid flow just by passing through it and provides an outgoing laminar mixed fluid flow. The vortex reducer [11] could be located in or near the downstream outlet [4] of the conduit [2]. Preferably, the vortex reducer [11] has a section adapted to the section of the conduit [2], having no mobile part and has several rectilinear holes [12] parallel to the longitudinal axis of the conduit [2] (FIGS. 1 and 4). Preferably all the holes are cylindrically-shaped and more preferably they are of same diameter. Flow of the fluid through the vortex reducer [11] is completed over a short distance. The number and the diameter of holes are adjusted to obtain from about 10% to about 50% of fluid flow obstruction, preferably from about 20% to about 40%, more preferably from about 25% to about 35%, and more particularly about 30%.

The fluid flow obstruction, expressed in percentage, is calculated by the following formula: $(X-Y)/X$ wherein X is the surface of the section of the vortex reducer, Y is the total of surfaces of holes of the vortex reducer.

The length of the holes of the vortex reducer is preferably at least equal to twice the diameter of a hole. The residence time inside the vortex reducer depends on the vortex reducer length and the fluid flow rate. The distance between the pipe outlet (or the nozzle if used) and the vortex reducer in a mixing device according to the invention may be as short as technically possible to avoid too long shearing a suspension of cells already lysed.

As soon as the cell suspension and the lysing solution mix together, the lysis starts. The mixing step duration is about 10 seconds or less, preferably about 5 seconds or less, more preferably about 2 seconds or less. Those skilled in the art know how to determine the distance between the pipe outlet (or the nozzle if used) and the vortex reducer to adapt the mixing step duration.

The possibility to use a vortex reducer is particularly advantageous to obtain an outgoing fluid laminar flow, avoiding the shearing of sensitive intracellular components present into the cell lysate. A further advantage of the vortex reducer is to divide the process into two distinct zones, the mixing zone and the contact zone. Upstream of the vortex reducer, turbulences created by the injection of additional fluids at a high linear speed in the fluid circulating into the conduit provide enough energy for the mixing of these fluids together, creating a very efficient mixing zone. The mixing zone stands between the pipe outlet [3] and the vortex reducer [11] if used or between the pipe outlet [3] and the downstream outlet [4] of the mixing device. The lysis of the cells occurs substantially between the pipe outlet [3] and the downstream outlet [4] of the conduit. Downstream of the vortex reducer, there is no more shearing force affecting the stability of the intracellular biological compound of interest liberated from the lysed cells, limiting the release of impurities and allowing degradation of the impurities, substantially through a contact pipe, until the addition of a neutralizing solution. The degradation of impurities occurs substantially in the contact zone standing between the downstream outlet [4] of the conduit and the addition of the neutralizing solution through the neutralizing solution connector.

According to a preferred embodiment, the mixing device of the invention is composed of a conduit [2] having an upstream inlet [6] and a downstream outlet [4], a pipe [1] with an inlet [5] and having an outlet [3] aligned with longitudinal axis of the conduit [2] and directed in co-flow or in counter-flow (FIG. 1), and by a vortex reducer [11] located in or near the downstream outlet [4] of the conduit [2].

According to another preferred embodiment, the mixing device of the invention is composed of a conduit [2] having an upstream inlet [6] and a downstream outlet [4], a pipe [1] with an inlet [5] and having an outlet ending with a spray nozzle [10] aligned with longitudinal axis of the conduit [2] and directed in co-flow or in counter-flow, and by a vortex reducer [11] located in or near the downstream outlet [4] of the conduit [2].

Optionally, the mixing device of the present invention may further comprise an impact target [13], located at a very short distance from the outlet [3] of the pipe [1]. This impact target provides impact forces to one or more additional fluids passing though the pipe [1] and impacting the target.

The linear speeds ratio may be advantageous to break up the cell aggregates present in cell suspensions. A breaking up of aggregates before contact with the lysing solution, allows a quicker action of the lysing solution and a better contact to all the surface of the cells, due to the fact that fewer cells may be hidden inside aggregates.

Without being bound by the theory, the impact may also be helpful for the breaking up of cell aggregates and may weaken the cellular membranes, capsules or walls and facilitate the action of the lysing solution.

The impact target [13] may be a plate located inside the conduit and closely in front of the pipe outlet [3]. "Closely" means that the impact target is at enough close range from the pipe outlet or nozzle to be hit by the additional fluid jet and to spread out this jet. Alternately, the impact target [13] may be a part of the mixing device, in particular the side wall [8] of the conduit [2]. In this case, the pipe outlet [3] may not be aligned with the longitudinal axis of the conduit [2] but closely located and oriented to this part of the mixing device, in particular to the side wall [8] of the conduit [2].

As seen in FIG. 5, in one particular embodiment of this option, the pipe outlet [3] is composed of an impact spray nozzle [14] itself including the impact target [13]. Such impact spray nozzles are available on the market (e.g. from Delavan® Spray Technologies; from Spraying Systems Co.®; Bete® Fog Nozzle Inc.; Nozzle Network Company Ltd.). One skilled in the art is able to select an impact spray nozzle and to use it according to the invention in a liquid environment, e.g. for the injection of a fluid into a second fluid. When an impact spray nozzle is used, the ratio of linear speeds is from about 100 to about 6000, in particular from about 100 to about 3000, more particularly from about 100 to about 2000, preferably from about 300 to about 1000 and more preferably from about 400 to about 700.

According to a preferred embodiment, the mixing device of the invention is composed of a conduit [2] having an upstream inlet [6] and a downstream outlet [4], a pipe [1] with an inlet [5] and an outlet ending with an impact spray nozzle [14] aligned with longitudinal axis of the conduit [2] and directed in co-flow (FIG. 3) or in counter-flow.

According to another preferred embodiment, the mixing device of the invention is composed of a conduit [2] having an upstream inlet [6] and a downstream outlet [4], a pipe [1] with an inlet [5] and an outlet ending with an impact spray nozzle [14] aligned with longitudinal axis of the conduit [2] and directed in co-flow or in counter-flow, and by a vortex reducer [11] located in or near the downstream outlet [4] of the conduit [2].

In a most preferred embodiment, the mixing device of the invention is composed of a conduit [2] having an upstream inlet [6] and a downstream outlet [4], a pipe [1] with an inlet [5] and an outlet ending with an impact spray nozzle [14] aligned with longitudinal axis of the conduit [2] and directed in co-flow or in counter-flow, and by a vortex reducer [11] located in or near the downstream outlet [4] of the conduit [2] and having a mixing step duration of about 2 seconds.

The present invention discloses flow-through methods for preparing a cell lysate containing a biological compound of interest. These methods comprise the culture of cells containing cellular compounds of interest, the harvest of these cells, a mixing and lysis step according to the present invention and further steps for extracting, purifying and isolating cellular compounds of interest from lysed cells.

The term of "cell" encompasses any cell capable of producing and containing any biological compound of interest. The cell may be selected from the group constituted by prokaryotic cells, notably bacteria and particularly *Escherichia coli* (*E. coli*), and from the group constituted by eukaryotic cells, notably yeast, insect cells, mammal cells. The biological compounds of interest are proteins, RNAs, DNAs, viruses or phages, and preferably plasmid DNAs, more preferably supercoiled plasmid DNAs. The cells are produced and harvested by well-known techniques. Preferably the cells are produced by fermentation. In a preferred embodiment, the cells are *E. coli* with high copy number of plasmid DNAs produced at high density by batch (O'Kennedy R. D. et al., Biotechnol. Appl. Biochem., 2003, 37(1): 83-90) or fed-batch fermentation (Jones R. C. and Anthony R. M., European J. Appl. Microbiol., 1977, 4: 87-92).

The cells are harvested by any means known by the persons skilled in the art, in particular filtration or centrifugation. Preferably, the cells are harvested, concentrated by continuous flow centrifugation, in particular by disk stack continuous flow centrifugation (WO-A-00/05358). Further the cell pellet is resuspended in a buffer (e.g. Tris-EDTA/glucose buffer, see Birnboim and Doly, Nucleic Acids Res., 1979, 7, 1513-1523). Further the cells may be stored in a refrigerated form or in a frozen form.

The cell suspension and the lysing solution are mixed together in continuous flow by passage through the mixing device according to the invention. In alternative embodiments, the pipe outlet is ended by a spray nozzle or by an impact spray nozzle.

The additional fluids are preferably cell suspensions, in particular different cell suspensions in case of several additional fluids. Each cell suspension comprises cells containing biological compounds of interest, in particular plasmids, which compounds or plasmids are different from one cell suspension to another one. This allows the mixing of different cell suspensions, and the harvest of a mixture containing different biological compounds of interest, in particular different plasmids. The type of cells may be different from one cell suspension to another one (e.g. prokaryotic cells, notably bacteria and particularly *Escherichia coli* (*E. coli*), eukaryotic cells, notably yeast, insect cells, mammalian cells).

In a first embodiment, the lysing solution comprises at least one chaotropic agent with or without at least one surfactant. A chaotropic agent is a chemical that can disrupt the hydrogen bonding structure of water. In concentrated solutions they can denature proteins because they reduce the hydrophobic effect. Chaotropic agents include for example urea, guanidine hydrochloride. A surfactant is a molecule with a hydrophilic head and a hydrophobic end. A surfactant is capable of reducing the surface tension of a liquid in which it is dissolved. Surfactants may include, but are not limited to polysorbate surfactants (e.g., Tween®), detergents (e.g., Brij®), and non-ionic surfactants (e.g., Triton®) and/or combinations thereof.

In a second embodiment, the lysing solution comprises at least one organic solvent. Organic solvents are chemicals capable to dissolve organic matter. Organic solvents include in particular phenol and chloroform.

In a preferred embodiment, the lysing solution comprises at least one alkali agent and at least one detergent compound. The alkali agent refers to any substance that provides a pH greater than about 8 when a sufficient amount of the substance is added to water. Alkali agents include for example sodium hydroxide (NaOH), potassium hydroxide (KOH), or lithium hydroxide (LiOH). The detergent compound refers to any amphipathic agent, whether neutral, anionic, cationic or zwitterionic. Detergent compounds include sodium dodecyl sulfate (SDS), ethylene oxide/propylene oxide block copolymers (e.g. Pluronic®), polyoxyethylene ether (e.g. Brij®), polyethylene glycol sorbitan (e.g. Tween®). Preferably the lysing solution comprises sodium hydroxide and SDS (see Birnboim and Doly, Nucleic Acids Res., 1979, 7, 1513-1523). The NaOH concentration is preferably about 0.1 N to about 0.3 N, and more preferably about 0.2 N. The SDS concentration is preferably about 0.1% to about 5%, and more preferably about 1%.

Advantageously the lysing solution according to the present invention does not contain any enzyme, in particular no lysozyme or RNase.

Commonly for one volume of cell suspension, one volume of the lysing solution is preferably added.

A neutralizing solution is added in a continuous flow to the cell lysate to neutralize the lysing agents. The neutralizing solution contains an acidic agent such as acetic acid, and a salt, such as potassium acetate or ammonium acetate. Preferably the neutralizing solution contains potassium acetate and acetic acid. More preferably, the neutralizing solution contains about 3 M potassium acetate and 2 M acetic acid.

The neutralizing solution is injected through any connector, in particular an inlet, a T or a Y connector, located immediately downstream of the mixing device according to the invention.

One skilled in the art can control the quantity of neutralizing solution by adapting the section of the connector and/or by adjusting the flow rate of the neutralizing solution. Preferably, for four volumes of cell lysate, three volumes of the neutralizing solution are added.

This neutralization prevents a prolonged action of the lysing agents, which may be responsible of the denaturation of the biological compound of interest and the formation of impurities. The neutralization allows the precipitation of the impurities, in particular the precipitation of genomic DNAs.

Preferably, the device of the present invention may further comprise a pipe, located downstream of the conduit outlet (or downstream of the vortex reducer when used) and upstream of the connector through which the neutralizing solution is added. This pipe is called contact pipe. The contact pipe is used to degrade the impurities present in the cell lysate, in particular endotoxins and RNAs. The length of this contact pipe determines the residence time of the mixed fluids passing through it and thus the duration of the contact between the lysing solution and the cell lysate and finally degradation of the impurities. The contact pipe constitutes the contact zone and is the main element of the contact step. The persons skilled in the art can without undue experimentations adapt the length of the contact pipe to the duration of the contact according to the nature and concentration of the impurities present in each cell lysate. Preferably the length of the contact pipe is enough for a contact step from about 1 second to about 10 minutes, more preferably from about 1 second to about 5 minutes, and more particularly from about 1 sec to about 2 minutes. In this case, the neutralizing solution is injected through any connector, in particular an inlet, a T or a Y connector, located immediately downstream of the contact pipe.

After lysis and neutralization of the lysing solution, the impurities must be removed from the biological compound of interest by any means known by the persons skilled in the art.

In case of plasmid DNAs recovery as biological compound of interest, the addition of a precipitating composition provides the precipitation of solid impurities, in particular the cell debris and some cellular components like RNAs. The precipitating composition contains preferably calcium chloride ($CaCl_2$). Preferably the $CaCl_2$ precipitating composition is added to the neutralized lysate in continuous flow through a connector. The precipitating composition connector may be any connector, in particular an inlet, a T or Y connector, or a second mixing device according to the present invention. The final concentration of $CaCl_2$ in the lysate after addition may be from about 0.05 M to about 0.6 M. The precipitated impurities and the clarified lysate may be separated by decantation and/or centrifugation and/or filtration. Preferably, the precipitated impurities and the clarified lysate may be separated by decantation, followed by a continuous flow centrifugation, a depth filtration, preferably on diatomaceous earth based filter, with a cutoff between 2-0.1.mu.m, preferably with a cutoff between 1-0.2.mu.m. The clarified lysate contains the plasmid DNAs. At this stage, the product is ready for purification.

The clarified lysate may be then concentrated by ultrafiltration (e.g. with a cutoff less than or equal to 300 kDa) and diafiltered to change the solvent.

The concentrated clarified lysate may be subjected to size-exclusion chromatography using but not limited to chromatography resins (e.g. Sephacryl™ S-400HR), Sephacryl™ S-1000C, or Sepharose™ 4FF, or Sepharose™ 6FF from Amersham Biosciences Corp., Piscataway, N.J., USA; Toyopearl™ HW65 or Toyopearl™ HW75 from Tosoh Biosciences, Superflow6™ from Sterogene) and/or ion exchange chromatography (e.g. Fractogel® EMD DEAE or Fractogel® EMD TMAE from Merck KGaA, Darmstadt, Germany; Q Ceramic Hyper DF from Biosepra; Q Macroprep™ from Biorad; Q Sepharose™ from Amersham Biosciences Corp., Piscataway, N.J., USA) and/or hydrophobic interaction chromatography to purify plasmid DNA (e.g. Octyl Sepharose™ from Amersham Biosciences Corp., Piscataway, N.J., USA) and/or hydroxyapatite (HA Macroprep™ from Biorad, see WO-A-97/35002; WO-A-02/095047). Preferably, the clarified lysate is purified by size-exclusion chromatography.

Further the purified plasmid DNA may be concentrated by ultrafiltration and/or diafiltration. Finally the plasmid DNA is sterilized by sterile filtration (e.g. with filter having a cutoff of 0.22.mu.m).

Advantageously, the device according to the invention may be used in a continuous flow-through mode that processes rapidly large volumes of fluids. The fluid flow rates may be adapted to increase the quantity of fluids to be processed in a given time without changing the device. For further scale-up, the device may be easily adjusted by simple modification of the size of the conduit section and/or of the pipe outlet section. The device of the invention allows flexibility and easy scale-up process.

The device of the present invention can also be adapted to known processes for isolating biological compounds of interest (e.g., DNA, RNA and proteins). For example, the device described herein could be applied to the methods of U.S. Pat. Nos. 5,945,515; 5,346,994 and 4,843,155 by one of ordinary skill in the art.

The present invention encompasses the biological compounds of interest obtained by the process of the invention, in particular the plasmid DNAs obtained by the process of the invention.

The invention will now be further described by way of the following non-limiting examples.

Example 1

*Escherichia coli* (SCS1 strain, catalogue number # 200231 from Stratagene®) bacteria with high copy number of plasmid DNAs (a plasmid encoding rabies genes) were cultured to high density by fermentation. After culture, the bacteria were harvested.

*E. coli* bacteria were concentrated by disk stack continuous flow centrifugation using a CSC-6 centrifuge (Westfalia) at 70 L/h.

The bacteria were stored frozen.

When enough bacteria were produced, the frozen pools were thawed, mixed and diluted by addition of S1 buffer (Tris 25 mM, EDTA 10 mM, glucose 50 mM, pH 7.2).

A mixing device was designed with a conduit (100 mm of length and 22 mm of internal diameter), with a fine atomizing spray nozzle such as a PJ40 impact spray nozzle or fog nozzle (e.g., Bete® Fog Nozzle Inc.) oriented in co-flow direction of the fluid passing through the conduit, and followed by a contact pipe (cylindrically-shaped, 25 mm of internal diameter, 6.5 m of length, for about 140 seconds of contact duration), by a T connector and by a second contact pipe.

The bacterial suspension was injected through the PJ40 impact spray nozzle with a flow rate of about 40 L/h. A lysing solution (NaOH 0.2 N, SDS 1%) was injected through the conduit with a flow rate of about 40 L/h. A neutralizing solution (potassium acetate 3 M and acetic acid 2 M) was injected through the T connector with a flow rate of about 60 L/h for the neutralization of the lysing solution and for the precipitation of impurities, in particular genomic DNAs.

The mixing duration with this mixing device was less than 5 seconds and the contact duration between the cell suspension and the lysing solution was 140 seconds.

The linear speed of the lysing solution passing through the conduit of this mixing device was about 3 cm/sec, the linear speed of the bacterial suspension passing through the impact spray nozzle of this mixing device was about 14 m/sec. The linear speed ratio was also about 500.

The cell lysate was then treated by $CaCl_2$ (at a final concentration of 0.4 M in the mixture) to precipitate impurities in particular RNAs and endotoxins. After centrifugation and filtration, the clarified lysate contains the plasmid DNA.

The clarified lysate was then concentrated by ultrafiltration with a 300 kDa cutoff membrane. The concentrated solution was diafiltered to change the solvent for a chromatography buffer.

The clarified lysate was subjected to size-exclusion chromatography.

1.31 mg of plasmid DNA per gram of wet biomass were obtained with 83% of supercoiled pDNA.

Example 2

After culture as described in example 1, the same SCS1 *E. coli* bacteria were harvested.

*E. coli* bacteria were concentrated by disk stack continuous flow centrifugation using a CSC-6 centrifuge (Wesffalia) at 70 L/h. Further the cell pellet was resuspended in S1 buffer (Tris 25 mM, EDTA 10 mM, glucose 50 mM, pH 7.2).

The bacteria were stored frozen.

When enough bacteria were produced, the frozen pools were thawed, mixed and diluted by addition of S1 buffer.

A mixing device was designed with a conduit (100 mm of length and 22 mm of internal diameter), with a fine atomizing spray nozzle such as a PJ40 spray nozzle (Bete® Fog Nozzle Inc.) oriented in co-flow direction of the fluid passing through the conduit, and followed by a contact pipe (cylindrically-shaped, 25 mm of internal diameter, 3.4 m of length, for about 60 seconds of contact duration), by a T connector and by a second contact pipe.

A second mixing device was designed with a conduit (100 mm of length and 22 mm of internal diameter), with a fine atomizing spray nozzle such as a PJ40 spray nozzle (Bete® Fog Nozzle Inc.) oriented in co-flow direction of the fluid passing through the conduit, and followed by a T connector and by a second contact pipe.

A comparative experiment has been done with that mixing device with or without the contact pipe.

For each mixing device, the bacterial suspension was injected through the PJ40 spray nozzle with a flow rate of about 50 L/h. A lysing solution (NaOH 0.2N, SDS 1%) was injected through the conduit with a flow rate of about 50 L/h. A neutralizing solution (potassium acetate 3 M and acetic acid 2 M) was injected through the T connector with a flow rate of about 75 L/h for the neutralization of the lysing solution and for the precipitation of impurities, in particular genomic DNAs.

The mixing duration with that mixing device was less than 5 seconds.

The linear speed of the lysing solution passing through the conduit of the mixing device was about 3.6 cm/sec, the linear speed of the bacterial suspension passing through the spray nozzle was about 17.7 m/sec. The linear speed ratio was also about 500.

Samples of neutralized alkaline lysates were centrifuged by bucket centrifugation under the same conditions between samples.

Supernatants were analysed for quantities of pDNA, percentage of supercoiled PDNA and quantity of endotoxins (expressed in international unit of endotoxin per milliliter of culture). These results are presented in the following table: TABLE-US 00001 Contact pDNA (mg/g % of Endotoxins duration of wet supercoiled (IU/ml of (seconds) biomass) pDNA culture) With a 60 1.60 96 592 contact pipe Without a Not relevant 1.45 93 7630 contact pipe These results show that the absence of contact pipe leads to similar plasmid DNA yields, but does not reduce the quantity of endotoxins. This demonstrates the high efficiency of the mixing device of the present invention.

Example 3

*Escherichia coli* (SCS1 strain, catalogue number # 200231 from Stratagene®) bacteria with high copy number of plasmid DNAs (a plasmid encoding rabies genes) were cultured to high density by fermentation. After culture, the bacteria were harvested.

*E. coli* bacteria were concentrated by disk stack continuous flow centrifugation using a CSC-6 centrifuge (Westfalia) at 70 L/h.

The bacteria were stored frozen.

When enough bacteria were produced, the frozen pools were thawed, mixed and diluted by addition of S1 buffer (Tris 25 mM, EDTA 10 mM, glucose 50 mM, pH 7.2).

The continuous alkaline lysis process described in example 1 was used to produce neutralized alkaline lysates with or without contact pipe, with a flow rate of 50 L/h of lysing solution, 50 L/h of bacterial suspension and 75 L/h of neutralizing solution.

Samples of neutralized alkaline and $CaCl_2$ treated lysates were centrifuged by bucket centrifugation under the same conditions between samples.

Supernatants were analysed for quantities of pDNA and percentage of supercoiled pDNA. These results are presented in the following table: TABLE-US 00002% of Contact duration pDNA (mg/g of supercoiled (seconds) wet biomass) pDNA With a 60 1.45 93 contact pipe Without a Not relevant 1.35 95 contact pipe These results after CaCl.sub.2 treatment show that the absence of contact pipe leads to the same plasmid DNA yield. This demonstrates the high efficiency of the mixing device of the present invention.

Example 4

After culture as described in example 1, the SCSI *E. coli* bacteria were harvested.

*E. coli* bacteria were concentrated by disk stack continuous flow centrifugation using a CSC-6 centrifuge (Wesffalia) at 70 L/h. Further the cell pellet was resuspended in S1 buffer (Tris 25 mM, EDTA 10 mM, glucose 50 mM, pH 7.2).

The bacteria were stored frozen.

When enough bacteria were produced, the frozen pools were thawed, mixed and diluted by addition of S1 buffer.

A mixing device was designed with a conduit (100 mm of length and 35 mm of internal diameter), with a fine atomizing spray nozzle, such as a P54 impact spray nozzle (Bete® Fog Nozzle Inc.) oriented in co-flow direction of the fluid passing through the conduit, with a vortex reducer (50 mm of length and 36 mm of diameter, located right downstream the conduit, and having 26 holes of 17 mm of length and 5 mm of diameter each). The mixing device was followed by a contact pipe (cylindrically-shaped, 32 mm of internal diameter, 3.3 m of length, for 60 seconds of contact duration), by a T connector and by a second contact pipe.

The bacterial suspension was injected through the P54 impact spray nozzle with a flow rate of about 80 L/h. A lysing solution (NaOH 0.2 N, SDS 1%) was injected through the conduit with a flow rate of about 80 L/h. A neutralizing solution (potassium acetate 3 M and acetic acid 2 M) was injected through the T connector with a flow rate of about 120 L/h for the neutralization of the lysing solution and for the precipitation of impurities, in particular genomic DNAs.

The mixing duration with this mixing device was less than 5 seconds and the contact duration between the cell suspension and the lysing solution was about 60 seconds.

The linear speed of the lysing solution passing through the conduit of this mixing device was about 2.3 cm/sec, the linear speed of the bacterial suspension passing through the impact spray nozzle of this mixing device was about 15 m/sec. The linear speed ratio was also about 650.

The cell lysate was then treated by CaCl.sub.2 (at a final concentration of 0.2M in the mixture) to precipitate impurities in particular RNAs and endotoxins. The separation between the precipitated impurities and the clarified lysate was done by bucket centrifugation.

1.22 mg of plasmid DNA per gram of wet biomass were obtained, with 95% of supercoiled PDNA.

The invention shall now be further described by the following numbered paragraphs:

1. A device for mixing a lysing solution with one or more additional fluids, wherein at least one of the additional fluids comprises suspended cells to be lysed, comprising:

a conduit through which the lysing solution circulates with a linear speed equal to or less than about 2 m/sec;

one or more pipes through which one or more additional fluids are injected into the conduit with a linear speed from about 1 m/sec to about 150 m/sec, wherein the ratio of linear speeds measured at the pipe outlet between the additional fluid linear speed and the lysing solution linear speed is from about 100 to about 15000 and causes substantial mixing of the lysing solution with one or more additional fluids; and an outlet through which a outgoing fluid comes out of the conduit, wherein the outgoing fluid is composed of the lysing solution and one or more additional fluids after having been substantially mixed.

2. A device for mixing a lysing solution with one or more additional fluids, wherein at least one of the additional fluids comprises suspended cells to be lysed, comprising:

a conduit through which the lysing solution circulates with a linear speed equal to or less than about 2 m/sec;

one or more pipes through which one or more additional fluids are injected into the conduit with a linear speed from about 1 m/sec to about 150 m/sec, wherein the ratio of linear speeds measured at the pipe outlet between the additional fluid linear speed and the lysing solution linear speed is from about 100 to about 15000 and causes substantial mixing of the lysing solution with one or more additional fluids;

an outlet through which a outgoing fluid comes out of the conduit, wherein the outgoing fluid is composed of the lysing solution and one or more additional fluids after having been substantially mixed; and a vortex reducer located near or in the outlet of the conduit, which reduces or suppresses any rotational velocity or any toric component of the outgoing fluid to obtain an outgoing laminar flow.

3. A device for mixing a lysing solution with one or more additional fluids, wherein at least one of the additional fluids comprises suspended cells to be lysed, comprising:

a conduit through which the lysing solution circulates with a linear speed equal to or less than about 2 m/sec;

one or more pipes ending by a spray nozzle through which one or more additional fluids are injected into the conduit with a linear speed from about 1 m/sec to about 150 m/sec, wherein the ratio of linear speeds measured at the spray nozzle outlet between the additional fluid linear speed and the lysing solution linear speed is from about 100 to about 6000 and causes substantial mixing of the lysing solution with one or more additional fluids; and an outlet through which a outgoing fluid comes out of the conduit, wherein the outgoing fluid is composed of the lysing solution and one or more additional fluids after having been substantially mixed.

4. A device for mixing a lysing solution with one or more additional fluids, wherein at least one of the additional fluids comprises suspended cells to be lysed, comprising:

a conduit through which the lysing solution circulates with a linear speed equal to or less than about 2 m/sec;

one or more pipes ending by a spray nozzle through which one or more additional fluids are injected into the conduit with a linear speed from about 1 m/sec to about 150 m/sec, wherein the ratio of linear speeds measured at the spray nozzle outlet between the additional fluid linear speed and the lysing solution linear speed is from about 100 to about 6000 and causes substantial mixing of the lysing solution with one or more additional fluids;

an outlet through which a outgoing fluid comes out of the conduit, wherein the outgoing fluid is composed of the lysing solution and one or more additional fluids after having been substantially mixed; and a vortex reducer located near or in the outlet of the conduit, which reduces or suppresses any rotational velocity or any tonic component of the outgoing fluid to obtain an outgoing laminar flow.

5. The device of paragraph 3 or 4, wherein the spray nozzle is an impact spray nozzle.

6. The device of paragraph 3 or 4, wherein the spray nozzle is oriented to a part of the mixing device, which part constitutes an impact target.

7. A flow-through method for preparing a biological lysate containing a biological compound of interest, comprising:
flow of a cell suspension and a lysing solution through the mixing device according to any one of the paragraphs 1 to 6 to allow substantially a complete mixing and a cell lysis without a permanent denaturing of the biological compounds of interest;
flow of the mixed fluids through an optional contact pipe to allow degradation of impurities;
neutralize the lysing solution by adding a neutralizing solution.

8. A scalable and flow-through alkaline lysing process for large scale plasmid DNA extraction, comprising:
flow of a cell suspension and an alkaline lysing solution through a mixing device according to the method of the paragraph 7 to allow substantially a complete mixing and a cell lysis without a permanent denaturing of the plasmid DNAs;
flow of the mixed fluids through an optional contact pipe to allow degradation of impurities;
neutralize the lysing solution by adding a neutralizing solution to the cell lysate;
precipitate impurities by adding a precipitating composition;
clarify the lysate by decantation and/or centrifugation and/or filtration.

9. A biological compound of interest obtained by the process of paragraph 7.

10. Plasmid DNAs obtained by the process of paragraph 8.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A lysis process comprising the steps of:
providing a flow of lysis solution in a first direction;
providing a flow of one or more additional fluids in a direction other than the direction of the flow of the lysis solution;
wherein at least one of the additional fluids comprises biological cells that produce and contain biological substances of interest including proteins, RNAs, DNAs, viruses, phages, and virus-like particles;
wherein the flow of the lysis solution and at least one of the additional fluids induces turbulence and shearing forces;
wherein the lysis solution and the cells are subjected to an intense shearing during a short time period of less than 10 seconds to mix the lysis solution and the cells and to lyse the cells without a permanent denaturing of the biological substances compounds of interest; wherein the biological substances compounds of interest include proteins, RNA, DNA, viruses, phages, and virus-like particles;
wherein the intensity of the shearing is sufficient to cause substantially complete mixing of said fluids and has a magnitude that is at least as large as that produced when the ratio of the linear speed of the one or more additional fluids to the linear speed of the lysis solution is 100 to 15000; and
passing a combined fluid that results from the lysis solution being mixed with the one or more additional fluids comprising the biological cells through a vortex reducer to reduce or suppress any rotational velocity or any toric component of the flow and to obtain a laminar flow.

2. The process of claim 1, wherein the flow of the lysis solution and one of the additional fluids to induce turbulence further comprises maximizing exposure of the cells to the lysis solution.

3. The process of claim 1, wherein the lysis solution and the one or more additional fluids have continuous flow rates.

4. The process of claim 1, wherein at least a portion of the cells to be lysed further comprises lysing the portion of the cells within a mixing zone.

5. The process of claim 1, wherein the lysis solution and the one or more additional fluids are mixed for less than 5 seconds.

6. The process of claim 1, wherein the lysis solution and the one or more additional fluids are mixed for less than 2 seconds.

7. A lysis process comprising the steps of:
providing a flow of lysis solution in a first direction; direction providing a flow of one or more additional fluids in a direction other than the direction of the lysis solution at a linear speed to induce turbulence;
wherein at least one of the additional fluids comprises biological cells that produce and contain proteins, RNAs, DNAs, viruses, phages, and virus-like particles;
wherein the flow of the lysis solution and the flow of at least one of the additional fluids forms a mixing zone;
wherein the lysis solution and the at least one of the additional fluids in the mixing zone is subjected to intense shearing during a short time period of less than 10 seconds to mix the lysis solution and the cells and to lyse the cells without a permanent denaturing of the biological substances of interest;
wherein the lysis of the cells occurs within the mixing zone;
wherein the lysed mixed fluid is passed through a vortex reducer to reduce or suppress any rotational velocity or any toric component of the flow and to obtain a laminar flow; and
wherein the intensity of the shearing is sufficient to cause substantially complete mixing of said fluids and has a magnitude that is at least as large as that produced when the ratio of the linear speed of the one or more additional fluids to the linear speed of the lysis solution is 100 to 15000.

* * * * *